United States Patent [19]

Allen et al.

[11] Patent Number: 4,737,360

[45] Date of Patent: Apr. 12, 1988

[54] SKIN CARE COMPOSITIONS

[75] Inventors: David W. Allen; Barbara Allen, both of Yellow Springs, Ohio

[73] Assignee: Cernitin America, Inc., Yellow Springs, Ohio

[21] Appl. No.: 821,943

[22] Filed: Jan. 24, 1986

[51] Int. Cl.⁴ .......................... A61K 7/44; A61K 7/48
[52] U.S. Cl. ................................. 424/60; 424/195.1; 514/844; 514/846; 514/847; 514/938
[58] Field of Search ........................... 424/59, 60, 195; 514/844, 846, 847, 938

[56] References Cited

FOREIGN PATENT DOCUMENTS 2443835  7/1980  France ............................... 514/844

OTHER PUBLICATIONS

Ando et al. (I), Chem. Abs., 1978, vol. 88, p. 65874z.
Ando et al. (II), Chem. Abs., 1978, vol. 88, p. 11754s.
Sato, Chem. Abs., 1977, vol. 87, pp. 172730a and 172729g.

*Primary Examiner*—Dale R. Ore
*Attorney, Agent, or Firm*—Biebel, French & Nauman

[57] ABSTRACT

Skin care compositions comprising a pollen extract and non-animal and non-mineral oils.

14 Claims, No Drawings

SKIN CARE COMPOSITIONS

The present invention relates to skin care compositions and, more particularly, to skin care compositions which are essentially free of animal products and mineral oils.

The consumer is becoming increasingly concerned with the composition of skin care and other cosmetic products which come into contact with and/or are absorbed by the skin. The skin care composition of the present invention have been designed in response to this concern. They are free of animal products, mineral oil, and artificial colors and perfumes and, at the same time, they provide desirable moisturizing and/or cleansing properties.

The skin care compositions of the present invention are oil-in-water emulsions containing a pollen extract and a blend of natural oils. The compositions of the present invention are designed for use as moisturizers, skin cleansers, as well as hand or body lotions.

A pollen extract useful in the present invention is available from AB Cernel of Engleholm Sweden under the designation Cernitin K Liquid. It is a composite flower pollen extract which has been microbiologically fermented. Other pollen extracts are also useful.

The oils used in the present invention are non-mineral, natural oils and are not animal products. The oils used herein are preferably seed or vegetable oils and can be selected from among sesame oil, peanut oil, safflower oil, jojoba oil, apricot seed oil, almond oil and mixtures thereof.

The compositions of the present invention contain natural fragrances such as a blend of anise, bay, cedar, clove, corriander, cubeb, cumin, elecampane, eucalyptus, ginger, marjoram and peppermint and/or commercially available fragrance blends such as Carruba Natural Fragrance #4804.

In addition to pollen extract, natural vegetable or seed oils and fragrance, the compositions may contain preservatives such as imidazolidinyl urea, UV screen such as 2-ethylhexyl 4-dimethylaminobenzoate, dispersing agents, lubricants, emollients, conditions, surfactants such as Tween 20 and Carbopol 934, etc.

The skin care compositions of the present invention are illustrated in more detail by the following non-limiting examples. The compositions were prepared in each instance by preparing the components indicated and blending them together. The weight percentages are based on the total composition.

EXAMPLE 1

A hand and body lotion was prepared by blending the following.

| Component | Weight Percent | Material |
|---|---|---|
| A | 2.80 | Stearic Acid |
|   | 2.00 | Cetyl Alcohol |
|   | 2.00 | Glyceryl Monostearate (SE) |
|   | 4.50 | Isopropyl Palmitate |
|   | 4.50 | Isopropyl Myristate |
|   | 0.10 | Sesame Oil |
|   | 0.10 | Propylparaben |
|   | 0.50 | Escalol 507 (2-ethylhexyl 4-dimethylamino benzoate) |
|   | 0.10 | Tocopherol |
|   | 0.10 | Jojoba Oil |
|   | 0.10 | Apricot Seed Oil |
| B | 72.39 | Water* |
|   | 0.20 | Methylparaben |
|   | 3.00 | Glycerine |
|   | 4.00 | Propylene Glycol |
|   | 1.00 | Triethanolamine (99%) |
|   | 0.50 | Crodafos SG (alkoxylated cetyl phosphate) (Croda, Inc.) |
|   | 0.10 | Aloe Vera Gel 1:1 |
|   | 0.25 | Citric Acid |
| C | 0.30 | Germall 115 (imidazolidinyl urea) (Sutton Lab, Inc.) |
|   | 1.00 | Water |
| D | 0.10 | Aromatherm #4** |
|   | 0.10 | DL - Panthenol |
|   | 0.01 | Sodium Pyrolidone carboxylic acid (Ajidew-N-50) |
|   | 0.05 | Pollen Extract |
|   | 0.20 | Carrubba Essence #4804 (Carrubba, Inc.) |

EXAMPLE 2

A penetration cream was prepared from the following.

| Component | Weight Percent | Material |
|---|---|---|
| A | 4.00 | Stearic Acid |
|   | 2.40 | Glyceral Monostearate (Pure) |
|   | 5.00 | Isopropyl Palmitate |
|   | 0.10 | Propyl Paraben |
|   | 1.10 | Glyceral Monostearate (SE) |
|   | 1.30 | Cetyl Alcohol |
|   | 0.50 | Escalol 507 (Van Dyke, Inc.) |
|   | 0.10 | Tocopherol |
|   | 0.10 | Jojoba Oil |
|   | 0.10 | Apricot Seed Oil |
| B | 78.85 | Water* |
|   | 0.20 | Methyl Paraben |
|   | 1.00 | Triethanolamine (99%) |
|   | 1.00 | Propylene Glycol |
|   | 2.00 | Glycerine |
|   | 0.10 | Aloe Vera Gel I:I |
|   | 0.25 | Citric Acid |
|   | 0.10 | Sorbitol |
| C | 0.30 | Germall 115 |
|   | 1.00 | Water |
| D | 0.10 | Aromatherm #4** |
|   | 0.10 | LD-Panthenol |
|   | 0.05 | Sodium PCA (Ajidew N-50) |
|   | 0.05 | Pollen Extract (Cernitin K liquid) |
|   | 0.20 | Carrubba Natural Fragrance #4804 |

EXAMPLE 3

A skin wash was prepared from the following.

| Component | Weight Percent | Material |
|---|---|---|
| A | 4.00 | Cetyl Alcohol |
|   | 10.00 | Stearyl Alcohol |
|   | 4.00 | Spermaceti Wax (cetyl esters) |
|   | 0.10 | Propylparaben |
|   | 0.10 | Tocopherol |
|   | 0.10 | Jojoba Oil |
|   | 0.10 | Apricot Seed Oil |
|   | 1.00 | Propylene Glycol Monostearate SE |
| B | 69.00 | Water* |
|   | 0.20 | Methylparaben |
|   | 9.00 | Glycerine |
|   | 0.70 | Sodium Lauryl Sulfate |

-continued

| Component | Weight Percent | Material |
|---|---|---|
| | 0.10 | Aloe Vera Gel 1:1 |
| C | 0.30 | Germall 115 |
| | 1.00 | Water |
| D | 0.05 | Sodium PCA (Ajidew N-50) |
| | 0.05 | Pollen Extract (Cernitin K Liquid) |
| | 0.20 | Carrubba Natural Fragrance #4804 |

Example 4

A deep cleaning milk was prepared from the following:

| Component | Weight Percent | Material |
|---|---|---|
| A | 3.50 | Stearic Acid |
| | 11.00 | Almond Oil (Sweet) |
| | 11.00 | Sesame Oil |
| | 4.00 | Arlacel 165 (glyceral stearat and PEG 100 Stearate) (Rugar M. Chemical) |
| | 0.10 | Propylparaben |
| | 0.25 | Cetyl Alcohol |
| | 0.10 | Tocopherol |
| | 0.10 | Apricot Seed Oil |
| | 0.10 | Jojoba Oil |
| B | 62.40 | Water* |
| | 0.20 | Methylparaben |
| | 0.10 | Aloe Vera Gel 1.1 |
| | 4.00 | Glycerine |
| | 0.80 | Triethanolamine (95%) |
| | 0.20 | Citric Acid |
| C | 0.30 | Germall 115 |
| | 1.00 | Water |
| D | 0.10 | Hyssop Extract (Carruba, Inc.) |
| | 0.15 | Allantoin |
| | 0.20 | DL-Panthanol |
| | 2 gm/300 Kilos | Biotin |
| | 0.05 | Sodium PCA (Ajidew N-50) |
| | 0.10 | Aromatherm #4** |
| | 0.05 | Pollen Extract (Cernitin K Liquid) |
| | 0.20 | Carrubba Natural Fragrance #4804 |

Example 5

A night moisture cream was prepared from the following:

| Component | Weight Percent | Material |
|---|---|---|
| | 3.00 | Glyceryl Monostearate (SE) |
| | 1.20 | Cetyl Alcohol |
| | 4.20 | Stearic Acid |
| | 2.50 | Peanut Oil |
| | 2.50 | Sesame Oil |
| | 5.00 | Safflower Oil |
| | 0.10 | Tocopherol |
| | 0.10 | Jojoba Oil |
| | 0.10 | Apricot Seed Oil |
| | 0.10 | Propylparaben |
| B | 68.65 | Water* |
| | 0.20 | Carbopol 934 (carboxy polymethylene) |
| | 0.20 | Methylparaben |
| | 5.00 | Sorbitol |
| | 2.00 | Propylene Glycol |
| | 1.00 | Triethanolamine (99%) |
| | 0.10 | Aloe Vera Gel 1:1 |
| | 0.25 | Citric Acid |
| | 2.00 | Glycerine |
| C | 0.30 | Germall 115 |

-continued

| Component | Weight Percent | Material |
|---|---|---|
| | 1.00 | Water |
| D | 0.10 | Aromatherm #4** |
| | 0.05 | Sodium PCA (Ajidew N-50) |
| | 0.10 | DL-Panthenol |
| | 0.05 | Pollen Extract (Cernitin K Liquid) |
| | 0.20 | Carrubba Fragrance #4804 |

Example 6

A protective moisture lotion was prepared from the following:

| Component | Weight Percent | Material |
|---|---|---|
| A | 4.00 | Stearic Acid |
| | 3.50 | Glyceryl Monostearate |
| | 0.20 | Cetyl Alcohol |
| | 0.30 | Paraffin |
| | 1.10 | Propylparaben |
| | 1.40 | Escalol 507 |
| | 0.10 | Tocopherol |
| | 0.10 | Jojoba Oil |
| | 0.10 | Apricot Seed Oil |
| | 0.20 | Silicone L-45 (dimethicone) |
| B | 86.90 | Water* |
| | 0.20 | Methylparaben |
| | 0.70 | Triethanolamine (99%) |
| | 0.10 | Sorbitol |
| | 0.10 | Aloe Vera Gel 1:1 |
| | 0.20 | Citric Acid |
| C | 0.30 | Germall 115 |
| | 1.00 | Water |
| D | 0.10 | DL Panthenol |
| | 0.05 | Sodium PCA (Ajidew N50) |
| | 0.05 | Pollen extract-Cernitink Liquid |
| | 0.5 g/50 kg | Biotin |
| | 0.10 | Aromatherm #4** |
| | 0.20 | Carruba Natural Fragrance #4804 |

Example 7

A skin toner was prepared from the following:

| Component | Weight Percent | Material |
|---|---|---|
| A | 15.00 | Witch Hazel |
| | 0.15 | Aromatherm #4 |
| B | 77.45 | Water* |
| | 4.00 | Glycerine |
| | 1.00 | Tween 20 |
| | 1.40 | Germaben II (diazolidinyl urea, methylparaben, propylparaben) (Sutton Lab.) |
| C | 0.50 | Niacinamide |
| | 0.05 | Pollen (Cernitin K Liquid) |
| | 0.10 | DL-Panthenol |
| | 0.05 | Sodium PCA (Ajidew N-50) |
| | 0.10 | Aloe Vera Gel 1:1 |
| | 0.20 | Carrubba Natural Fragrance #4804 |

Footnotes
*includes about 5% extra water for evaporation
**a blend of bay, anise, cedar, clove, coriander, cubeb, cumin, elecampane, eucalyptus, ginger, marjoram, peppermint snakeroot and wormwood available from Robert, Inc.

Having described the invention in detail and by reference to preferred embodiment thereof, it will be apparent that numerous variations and modifications are possible without departing from the spirit and scope of the following claims:

We claim:

1. An oil-in-H₂O emulsion skin care composition which is essentially free of animal and mineral oils comprising a pollen extract and a non-animal and non mineral-oil selected from the group consisting of peanut oil, sesame oil, safflower oil, jojoba oil, apricot seed oil, almond oil and mixtures thereof and aloe vera gel and an aqueous carrier.

2. The skin care composition of claim 1 wherein said composition further comprises natural fragrances.

3. The skin care composition of claim 2 wherein said non-animal and non-mineral oil comprises a mixture of sesame oil, jojoba oil, and apricot seed oil.

4. The skin care composition of claim 2 wherein said non-animal and non-mineral oil comprises a mixture of sesame oil, peanut oil, safflower oil, jojoba oil, and apricot seed oil.

5. The composition of claim 2 wherein said non-animal and non-mineral oil comprises a mixture of almond oil, sesame oil, apricot seed oil and jojoba oil.

6. The composition of claim 2 wherein said non-animal and non-mineral oil comprises jojoba oil, and apricot seed oil.

7. The composition of claim 2 wherein said non-animal and non-mineral oil comprises a mixture of jojoba oil and apricot seed oil.

8. A composition in accordance with claim 1 which is a hand and body lotion further comprising isopropyl palmitate, isopropyl myristate, propylene glycol, glycerine, stearic acid, triethanolamine, tocopherol, panthenol, sodium pyrrolidone carboxycic acid, imidazolidinyl urea, 2-ethylhexyl 4-dimenthylaminobenzoate, methylparaben, propylparaben, citric acid, and fragrances.

9. A composition in accordance with claim 1 which is a night moisturizer cream further comprising sorbitol, stearic acid, glyceryl monostearate, propylene glycol, glycerine, cetyl alcohol, triethanolamine, tocopherol, panthenol, sodium pyrrolidone carboxylic acid, imidazolidinyl urea, surfactant, citric acid, propylparaben, methylparaben, and fragrances.

10. A composition according to claim 1 which is a moisturizing lotion further comprising stearic acid, glyceryl monostearate, 2-ethylhexyl 4-dimethylaminobenzoate, sodium pyrrolidone carboxylic acid, tocopherol, panthenol, biotin, dimethicone, triethanolamine, paraffin, cetyl alcohol, sorbitol, citric acid, guaiazulene, methylparaben, and fragrances.

11. A composition according to claim 1 which is a moisturizing cream further comprising isopropyl palmitate, stearic acid, glyceryl monostearate, cetyl alcohol, triethanolamine, 2-ethylhexyl 4-dimethylaminobenzoate, propylene glycol, tocopherol, panthenol, sodium pyrrolidone carboxylic acid, imidazolidinyl urea, citric acid, sorbitol, propylparaben, methylparaben, and fragrances.

12. A composition according to claim 1 which is a skin toner further comprising witch hazel, glycerine, polysorbate 20, diazolidinyl urea, methylparaben, propylparaben, sodium pyrrolidone carboxylic acid, panthenol, niacinimide, and fragrances.

13. A composition according to claim 1 which is a cleansing milk further comprising glyceryl stearate, polyethylene glycol-100 stearate, glycerin, stearic acid, triethanolamine, tocopherol, panthenol, sodium pyrrolidone carboxylic acid, biotin, imidazolidinyl urea, hyssop extract, cetyl alcohol, allantoin, propylparaben, methylparaben, citric acid.

14. A composition according to claim 1 which is a skin wash further comprising stearyl alcohol, glycerine cetyl esters, cetyl alcohol, propylene glycol monostearate, sodium lauryl sulfate, alpha-tocopherol, sodium pyrrolidone carboxylic acid, imidazolidinyl urea, propylparaben, methylparaben, and fragrances.

* * * * *